United States Patent [19]

Caupin et al.

[11] Patent Number: 5,439,641

[45] Date of Patent: * Aug. 8, 1995

[54] UNDECYLENATE DEODORIZATION OF PAPER MILL EFFLUENTS

[75] Inventors: Henri-Jean Caupin, Versailles; Aim Menassa, Paris, both of France

[73] Assignees: Elf Atochem S.A., Puteaux; Delta Agro Industries, Paris, both of France

[*] Notice: The portion of the term of this patent subsequent to Aug. 16, 2011 has been disclaimed.

[21] Appl. No.: 98,105

[22] Filed: Jul. 28, 1993

[30] Foreign Application Priority Data

Jul. 30, 1992 [FR] France .................... 92 09457

[51] Int. Cl.⁶ .................................. A61L 9/01
[52] U.S. Cl. ........................ 422/5; 210/749; 210/916
[58] Field of Search ............... 472/5; 210/749, 751, 210/916

[56] References Cited

U.S. PATENT DOCUMENTS

| | | |
|---|---|---|
| 3,091,511 | 5/1963 | Calhoun . |
| 3,953,377 | 4/1976 | Naf .................................. 252/522 |
| 3,989,498 | 11/1976 | Cox ................................. 71/3 |
| 4,938,416 | 7/1990 | Bertrand et al. ................ 239/1 |

OTHER PUBLICATIONS

Price et al., "Sewage Treatment Plants Combat Odor Pollution Problems" Water & Sewage Works, Oct. 1978, pp. 64–69.

*Primary Examiner*—Timothy M. McMahon
*Attorney, Agent, or Firm*—Burns, Doane, Swecker & Mathis

[57] ABSTRACT

Malodorous/foul smelling paper mill effluents are deodorized by treating same with an effective deodorizing amount, e.g., from 0.01% to 5% by weight thereof, of an alkyl or polyoxyalkylene ester of undecylenic acid, for example methyl undecylenate or a polyoxyethylene undecylenate having 8 or 10 ethylene oxide recurring structural units.

10 Claims, 2 Drawing Sheets

UNDECYLENATE DEODORIZATION OF PAPER MILL EFFLUENTS

BACKGROUND OF THE INVENTION

1. Field of the Invention

The present invention relates to the deodorization of paper mill effluents, and, more especially, to the deodorization of paper mill effluents by treating same with an effective deodorizing amount of an alkyl/polyoxyalkylene ester of undecylenic acid.

2. Description of the Prior Art

Paper mills are prime sources of malodorous pollutants, originating in the effluents therefrom.

The reduction of emission risks from paper mill effluents constitutes the first step in combating foul odors and entails:

(a) removing the volatile pollutants contained in the effluent;

(b) limiting the formation of malodorous chemical compounds;

(c) limiting the physical phenomenon of conversion from aqueous to gaseous phases.

This struggle to eliminate disagreeable smells generally translates into the use of one or the other of the following techniques:

(i) injecting hydrogen peroxide into the effluent;

(ii) injecting pure oxygen into the effluent;

(iii) injecting an iron salt into the effluent (ferrous sulfate, complexing sulfides in the form of iron sulfide).

Nonetheless, given that the principal sources of uncontrolled disagreeable smells in paper mills are directly related to the formation of effluents therein, a satisfactory solution to this problem has to date eluded this art.

SUMMARY OF THE INVENTION

Accordingly, a major object of the present invention is the provision of a unique deodorant for paper mill effluents, said deodorant comprising an alkyl ester of undecylenic acid, or a polyoxyalkylene ester of undecylenic acid containing from 2 to 10 alkylene oxide recurring structural units.

DETAILED DESCRIPTION OF PREFERRED EMBODIMENTS OF THE INVENTION

More particularly according to the present invention, especially effective undecylenate deodorants are the $C_1$–$C_{12}$ alkyl esters and the polyoxyethylene, polyoxypropylene and poly(oxyethylene)/(oxypropylene) esters of undecylenic acid.

The undecylenate absorbants/deodorants according to the invention can be used either alone or in admixture, and such undecylenate deodorant(s) can be used as such, or in solution or suspension form, or can even be adsorbed onto a support such as, for example, clay particles.

Typically, the undecylenic esters are effective at a very low dose, for example on the order of 0.01% to 5% with respect to the weight of the effluent to be treated.

The curves shown in the attached Figures of Drawing evidence the effectiveness of representative alkyl and polyoxyethylene esters of undecylenic acid in deodorizing paper mill effluents containing malodorous pollutants especially comprising:

(1) $H_2S$ and sulfur-containing derivatives;

(2) fermentation products, which may or may not contain sulfur, of cellulose and of starch;

(3) putrefaction byproducts of dead animals contained in recycled paper and cardboard;

(4) disagreeable smells associated with the increase in the COD (chemical oxygen demand) and BOD (biological oxygen demand) of the waters recirculating at 100% in the process and diffusion of such smells during periods of contact of the waters with the surrounding atmosphere.

In these curves, the abscissa represents the degree of incorporation of the undecylenic ester (% by weight), the ordinate representing the degree of olfactory perception of the objectionable smell, the values 1 to 6 connoting, respectively: none, very weak, weak, average, strong and very strong.

In these Figures of Drawing, the upper curve corresponds to the smell of the effluent itself, the lower curve, optionally present, corresponding to the smell of the ester.

Figure 1:
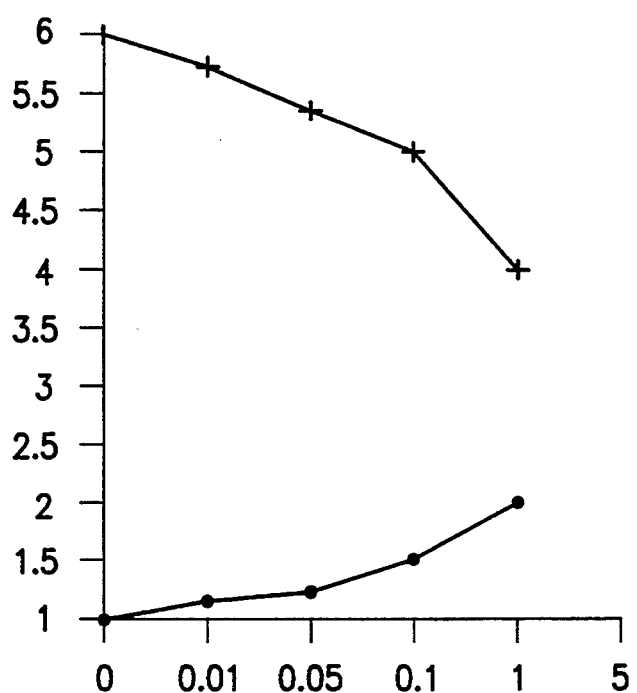
FIGS. 1 to 4 are graphs plotting the percentage of undecylate ester in the treated effluent versus the extent of olfactory perception of objectionable smells.
Figure 2:
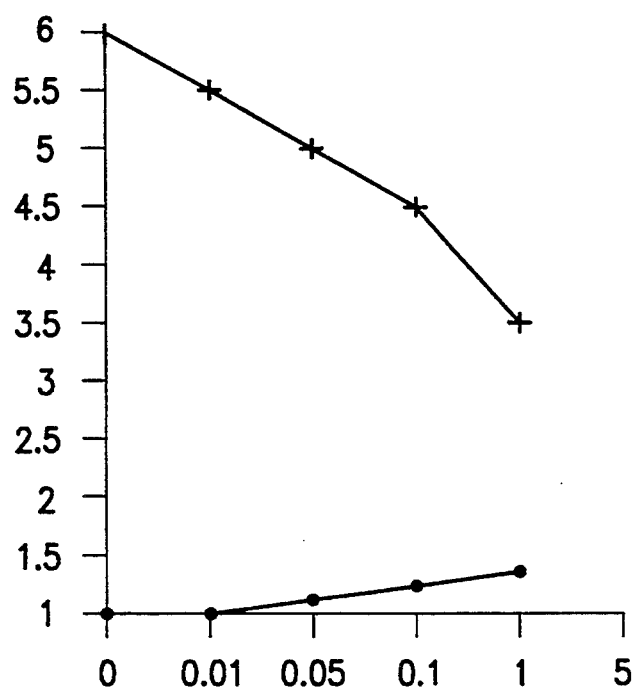
Figure 3:
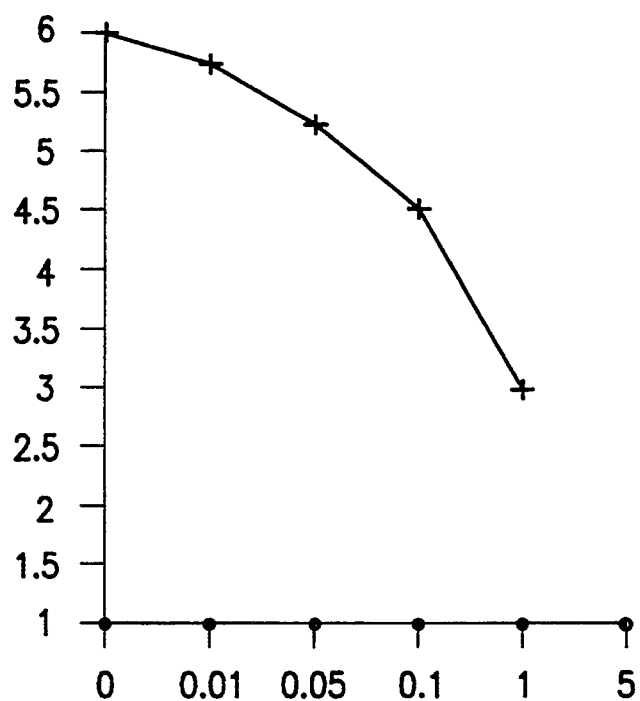

The curves of FIGS. 1 to 3, in accordance with the invention, indicate that the reduction in the perception of the smell of the effluent is not appreciably replaced by the perception of the smell associated with the ester itself.

Figure 4:
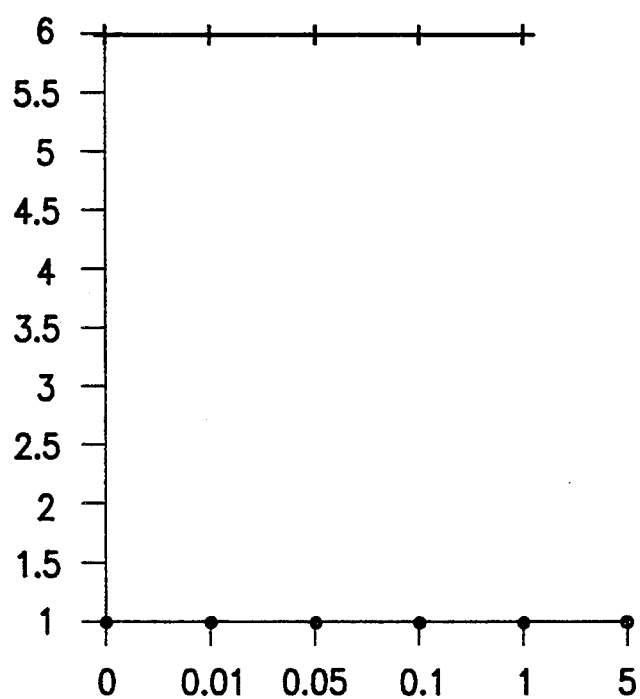

By way of comparison, FIG. 4 indicates that, with a polyoxyethylene ester of undecylenic acid containing 12 ethylene oxide recurring structural units, no reduction in the perception of the objectionable smell of the effluent is observed.

Curves 1 to 3 correspond, respectively, to methyl undecylenate, to the polyoxyethylene ester of undecylenic acid containing 8 ethylene oxide recurring structural units and to the ester of this same acid containing 10 ethylene oxide recurring structural units.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the deodorization of a malodorous paper mill effluent, comprising treating such effluent with an effective deodorizing amount of an alkyl or polyoxyalkylene ester of undecylenic acid, the polyoxyalkylene moiety of said undecylenate having from 2 to 10 alkylene oxide recurring structural units.

2. The process as defined by claim 1, said undecylenate deodorant comprising a $C_1$–$C_{12}$ alkyl ester of undecylenic acid.

3. The process as defined by claim 1, said undecylenate deodorant comprising a polyoxyalkylene ester of undecylenic acid.

4. The process as defined by claim 3, said undecylenate deodorant comprising a polyoxyethylene, polyoxypropylene or poly(oxyethylene)/(oxypropylene) ester of undecylenic acid.

5. The process as defined by claim 1, said undecylenate deodorant comprising a solution or suspension thereof.

6. The process as defined by claim 1, said undecylenate deodorant being sorbed onto support substrate therefor.

7. The process as defined by claim 1, comprising treating said paper mill effluent with from 0.01% to 5% by weight of said undecylenate deodorant.

8. The process as defined by claim 2, said undecylenate deodorant comprising methyl undecylenate.

9. The process as defined by claim 4, said undecylenate deodorant comprising a polyoxyethylene undecylenate having 8 ethylene oxide recurring structural units.

10. The process as defined by claim 4, said undecylenate deodorant comprising a polyoxyethylene undecylenate having 10 ethylene oxide recurring structural units.

* * * * *